US011857610B2

(12) United States Patent
Uknis et al.

(10) Patent No.: US 11,857,610 B2
(45) Date of Patent: Jan. 2, 2024

(54) METHODS FOR REDUCING RISK OF ONSET OF ACUTE GRAFT VERSUS HOST DISEASE AFTER HEMATOPOIETIC CELL TRANSPLANTATION

(71) Applicant: CSL BEHRING LLC, King of Prussia, PA (US)

(72) Inventors: Marc Uknis, Chadds Ford, PA (US); Christine Voigt, Devon, PA (US); Gautam Baheti, Chester Springs, PA (US); John Roberts, Chester Springs, PA (US)

(73) Assignee: CSL Behring LLC, King of Prussia, PA (US)

( * ) Notice: Subject to any disclaimer, the term of this patent is extended or adjusted under 35 U.S.C. 154(b) by 361 days.

(21) Appl. No.: 16/768,281

(22) PCT Filed: Nov. 30, 2018

(86) PCT No.: PCT/US2018/063179
§ 371 (c)(1),
(2) Date: May 29, 2020

(87) PCT Pub. No.: WO2019/108865
PCT Pub. Date: Jun. 6, 2019

(65) Prior Publication Data
US 2021/0008182 A1 Jan. 14, 2021

Related U.S. Application Data

(60) Provisional application No. 62/729,376, filed on Sep. 10, 2018, provisional application No. 62/593,446, filed on Dec. 1, 2017.

(51) Int. Cl.
*A61K 38/57* (2006.01)
*A61P 37/06* (2006.01)
*A61K 35/12* (2015.01)

(52) U.S. Cl.
CPC .............. *A61K 38/57* (2013.01); *A61K 35/12* (2013.01); *A61P 37/06* (2018.01); *A61K 2035/124* (2013.01)

(58) Field of Classification Search
CPC .. A61K 2035/124; A61K 35/12; A61K 38/57; A61P 37/06
See application file for complete search history.

(56) References Cited

U.S. PATENT DOCUMENTS

| | | |
|---|---|---|
| 9,457,070 B2 | 10/2016 | Dinarello et al. |
| 9,884,096 B2 | 2/2018 | Leland et al. |
| 2009/0028832 A1* | 1/2009 | Chung .................... A61P 35/00 424/93.7 |
| 2009/0105341 A1* | 4/2009 | Stanton .................. C12P 7/6472 435/243 |
| 2009/0118162 A1* | 5/2009 | Shapiro .................. A61K 35/39 435/1.1 |
| 2012/0045449 A1 | 2/2012 | Dinarello et al. |
| 2012/0178676 A1* | 7/2012 | Barrack .................. A61K 47/60 514/21.3 |
| 2015/0104410 A1* | 4/2015 | Eckelman ............ C07K 14/811 424/134.1 |

FOREIGN PATENT DOCUMENTS

| | | |
|---|---|---|
| WO | 2006133403 A2 | 12/2006 |
| WO | 2010088415 A2 | 8/2010 |
| WO | 2013003641 A2 | 1/2013 |
| WO | 2013106589 A1 | 7/2013 |
| WO | 2014160768 A1 | 10/2014 |
| WO | 2017117558 A1 | 7/2017 |

OTHER PUBLICATIONS

Giralt et al., Reduced Intensity Conditioning Regimen Workshop-Defining the Dose Spectrum: Report of a Workshop Convened by the Center for International Blood and Marrow Transplant Research, Biol. Blood Marrow Transplant, vol. 15(3):367-369 (Mar. 2009). (Year: 2009).*
Cutler et al., Tacrolimus/sirolimus vs tacrolimus/methotrexate as GVHD prophylaxis after matched, related donor allogeneic HCT, Blood, vol. 124(8):1372-1377 (Aug. 21, 2014) (Year: 2014).*
Gyurkocza et al., Conditioning regimens for hematopoietic cell transplantation: one size does not fit all, Blood, vol. 124(3):344-353 (Jul. 17, 2014) (Year: 2014).*
Ratanatharathorn et al., Phase III study comparing methotrexate and tacrolimus (prograf, FK506) with methotrexate and cyclosporine for graft-versus-host disease prophylaxis after HLA-identical sibling bone marrow transplantation, Blood, 92(7):2303-14 (Oct. 1, 1998) (Year: 1998).*
Nash et al., Phase 3 study comparing methotrexate and tacrolimus with methotrexate and cyclosporine for prophylaxis of acute graft-versus-host disease after marrow transplantation from unrelated donors, Blood, vol. 96(6):2062-8 (Sep. 15, 2000) (Year: 2000).*
Nash et al., Tacrolimus (FK506) alone or in combination with methotrexate or methylprednisolone for the prevention of acute graft-versus-host disease after marrow transplantation from HLA-matched siblings: a single-center study, Blood, vol. 85(12):3746-53 (Jun. 15, 1995) (Year: 1995).*
Przepiorka et al., Tacrolimus and minidose methotrexate for prevention of acute graft-versus-host disease after matched unrelated donor marrow transplantation, Blood, vol. 88(11):4383-9 (Dec. 1, 1996) (Year: 1996).*

(Continued)

*Primary Examiner* — Randall L Beane
(74) *Attorney, Agent, or Firm* — McNeill Baur PLLC

(57) ABSTRACT

This disclosure relates to methods for preventing or reducing the risk of development of graft versus host disease (GVHD) in patients receiving hematopoietic cell transplantation (HCT) by particular methods of administering alpha-1 antitrypsin (A1AT or AAT) to patients both prior to and following and HCT procedure. The disclosure also relates to specific methods of treating acute GVHD (aGVHD) after HCT with A1AT.

11 Claims, No Drawings

(56) References Cited

OTHER PUBLICATIONS

Rubio et al., The impact of HLA-matching on reduced intensity conditioning regimen unrelated donor allogeneic stem cell transplantation for acute myeloid leukemia in patients above 50 years—a report from the EBMT acute leukemia working party, Journal of Hematology & Oncology (2016) 9:65 (Year: 2016).*

Jacobsohn et al., "Acute graft versus host disease", Orphanet Journal of Rare Diseases, 2:35 (Sep. 4, 2007) (9 pages).

Jagasia et al., "Risk factors for acute GVHD and survival after hematopoietic cell transplantation", Blood, 119(1), pp. 296-307 (Jan. 5, 2012).

Jerkins et al., "Alpha-1-antitrypsin for the treatment of steroidrefractory acute gastrointestinal graft-versus-host diseas", Wiley AJH, E610-E611 (Jun. 30, 2017).

Kanakry et al., "Multi-Institutional Study of Post-Transplantation Cyclophosphamide as Single-Agent Graft-Versus-Host Disease Prophylaxis After Allogeneic Bone Marrow Transplantation Using Myeloablative Busulfan and Fludarabine Conditioning", Journal of Clinical Oncology, 22(31), pp. 3497-3505 (2014).

Lee et al., "IL-32-induced Inflammatory Cytokines Are Selectively Suppressed by alpha1-antitrypsin in Mouse Bone Marrow Cells", Immune Network, 17(2), pp. 116-120 (Apr. 2017).

MacMillian et al., "A Refined Risk Score for Acute Graft-versus-Host Disease that Predicts Response to Initial Therapy, Survival, and Transplant-Related Mortalit", Biol Blood Marrow Transplant, 21, pp. 761-767 (2015).

Magenau et al., "alpha1-Antitrypsin infusion for treatment of steroid-resistant acute graft-versus-host disease", Blood, 131(12), pp. 1372-1379 (Mar. 22, 2018).

Marcondes et al., "Alpha 1 Anti-Trypsin (AAT) Offers Potent Therapy for Steroid Resistant Gut Gvhd: Interim Results of a Phase I/II Clinical Study", Blood, 124(21), p. 3927 (2014) (4 pages).

Marcondes et al., "Alpha-1-Antitrypsin (AAT)-modified donor cells suppress GVHD but enhance the GVL effect: a role for mitochondrial bioenergetics", Blood, 124(18), pp. 2881-2891 (Oct. 30, 2014).

Marcondes et al., "Inhibition of IL-32 activation by alpha-1 antitrypsin suppresses alloreactivity and increases survival in an allogeneic murine marrow transplantation model", Blood, 118(18), pp. 5031-5039 (Nov. 3, 2011).

Marcondes et al., "Response of Steroid-Refractory Acute GVHD to alpha1-Antitrypsin", Biol Blood Marrow Transplant, 22, pp. 1596-1601 (2016).

Martin et al., "First- and Second-Line Systemic Treatment of Acute Graft-versus-Host Disease: Recommendations of the American Society of Blood and Marrow Transplantation", Biol Blood Marrow Transplant, 18, pp. 1150-1163 (2012).

Notification of Transmittal of the International Search Report and the Written Opinion of the International Searching Authority, or the Declaration, International Search Report and the Written Opinion of the International Searching Authority in International Application No. PCT/US2018/063179, dated Feb. 5, 2019 (12 pages).

Pasquini, M. C., "Impact of graft-versus-host disease on survival", Best Practice & Research Clinical Haematology, 21( 2), pp. 193-204 (2008).

Pavletic et al., "Are we making progress in GVHD prophylaxis and treatment?", Hematopoietic Stemcell Transplantation II: Toward Safer Allogeneic Transplantation, Hematology, pp. 251-264 (2012).

Rodriguez-Otero et al., "Fecal calprotectin and alpha-1 antitrypsin predict severity and response to corticosteroids in gastrointestinal graft-versus-host disease", Blood, 119(24); pp. 5909-5917 (Jun. 14, 2012).

Rowlings et al., "IBMTR Severity Index for grading acute graft-versus-host disease: retrospective comparison with Glucksberg grade", British Journal of Haematology, 97, pp. 855-864 (1997).

Silverman et al., "Alpha1-Antitrypsin Deficiency", The New England Journal of Medicine, 360(26), pp. 2749-2757 (Jun. 25, 2009).

Tawara et al., "Alpha-1-antitrypsin monotherapy reduces graft-versus-host disease after experimental allogeneic bone marrow transplantation", PNAS, 109(2), pp. 564-569 (Jan. 10, 2012).

Guidance for Industry: Estimating the Maximum Safe Starting Dose in Initial Clinical Trials for Therapeutics in Adult Healthy Volunteers, U.S. Department of Health and Human Services, Food and Drug Administration, Pharmacology and Toxicology, Jul. 2005.

Petrache, Irina et al., "Safety and efficacy of alpha-I-antitrypsin augmentation therapy in the treatment of patients with alpha-I-antitrypsin deficiency", Biologics: Targets & Therapy, 2009:3, 193-204.

NCT03805789, The Safety and Efficacy of Alpha-1 Antitrypsin (AAT) for the Prevention of Graft-Versus-host Disease (GVHD) in Patients Receiving Hematopoietic Cell Transplant (MODULAATE), dated Mar. 27, 2019, retrieved from the internet at: https://www.clinicaltrials.gov/study/NCT03805789?id=NCT03805789&rank=1 on Jun. 26, 2023.

Watkins, Benjamin et al., "Phase II Trial of Costimulation Blockade With Abatacept for Prevention of Acute GVHD", Journal of Clinical Oncology, vol. 39, Issue 17, Jan. 15, 2021, 1865-1878.

* cited by examiner

METHODS FOR REDUCING RISK OF ONSET OF ACUTE GRAFT VERSUS HOST DISEASE AFTER HEMATOPOIETIC CELL TRANSPLANTATION

CROSS-REFERENCE TO RELATED APPLICATIONS

This application is a national phase entry pursuant to 35 U.S.C. § 371 of International Application No. PCT/US2018/063179, filed Nov. 30, 2018, which claims priority to U.S. Provisional No. 62/729,376, filed Sep. 10, 2018, and U.S. Provisional No. 62/593,446, filed Dec. 1, 2017, the entire contents of which are incorporated by reference herein for all purposes.

TECHNICAL FIELD

This disclosure relates to methods for reducing the risk of development of graft versus host disease (GVHD) in patients receiving hematopoietic cell transplantation (HCT) by particular methods of administering alpha-1 antitrypsin (abbreviated A1AT or AAT or A1-PI) to patients both prior to and following a HCT procedure. The disclosure also relates to specific methods of treating acute GVHD (aGVHD) after HCT with A1AT.

BACKGROUND AND INTRODUCTION

Acute graft versus host disease (aGVHD) is a leading cause of death in patients undergoing hematopoietic cell transplantation (HCT), particularly allogeneic HCT. Most cases of aGVHD occur about 20-30 days after an HCT procedure, but aGVHD may occur up to 100 days after a procedure and the symptoms in some cases may persist beyond the 100 day mark. (See, e.g., C G Kanakry et al., *J. Clin. Oncol.* 32(31): 3497-3505 (2014); reporting a median of 34 days for the onset of Stage II to IV aGVHD symptoms with a range of 15-88 days.) aGVHD typically involves three organ systems: the skin, the gastrointestinal (GI) tract, and the liver. Symptoms include a maculopapular skin rash, diarrhea, vomiting, nausea, abdominal cramps, and jaundice due to hyperbilirubinemia. aGVHD is staged into four different grades or stages (I-IV) with IV being the most severe. Patients with Stage IV aGVHD have less than a 10% chance of survival, while those with Stage III have about a 30% survival rate, and those with Stage II and I have about an 80% and 90% chance of survival, respectively. (M C Pasquini, *Best Pract. Res. Clin. Hematol.* 21(2): 193-204 (2008).)

The risk of developing aGVHD after a HCT procedure depends on several factors including whether the donor is or is not related to the recipient, whether there is any mismatch in human leukocyte antigens (HLA) between the donor and recipient, and the type of pre-conditioning regimen that the recipient underwent prior to the HCT procedure. (See, e.g., D A Jacobsohn and G B Vogelsang, *Orphanet J. Rare Dis.* 2: 35 (doi.10.1186/1750-1172-2-35 (2007).) In addition to aGVHD's life-threatening nature, it has also proven difficult to treat, with about 50% of allogeneic HCT patients developing aGVHD even with the currently available treatments. (See Id.; S Z Pavletic & D H Fowler *Hematology Am. Soc. Hematol. Educ. Program* 2012: 251-65 (2012).) Current treatments focus, for example, on steroids such as methylprednisone and methylprednisolone as well as immunosuppressants such as methotrexate and calcineurin inhibitors. Not only do these treatments show limited success, their T cell suppressive activity risks negatively affecting the HCT graft. Thus, patients need other approaches to treating aGVHD and also preventing its onset after a HCT procedure that should not negatively impact the HCT graft.

Alpha-1 antitrypsin (A1AT) is a protease inhibitor and member of the serpin family of proteins. It is currently indicated for A1AT deficiency replacement therapy, for example at weekly dosages of 60 mg/kg. A1AT binds to enzymatic targets such as neutrophil elastase and has been shown to have anti-inflammatory, anti-neutrophil influx and activation, and anti-apoptotic effects on cells. Furthermore, A1AT is not a T-cell suppressant and instead supports a tolerogenic hematopoietic profile. The present disclosure relates, inter alia, to particular methods and dosage regimes using relatively high dosages of A1AT both prior to and following an HCT procedure for reducing the risk of onset of aGVHD after the procedure.

SUMMARY

The present disclosure includes methods of reducing the risk of onset of acute graft versus host disease (aGVHD) in a subject receiving hematopoietic cell transplantation (HCT) comprising administering alpha-1 antitrypsin (A1AT) according to the following schedule: (a) administering a dose of at least 120 mg/kg A1AT to the subject at least one day prior to an HCT procedure; (b) administering a dose of at least 90 mg/kg A1AT to the subject at least twice weekly following HCT for at least 4 weeks, which may optionally be followed by a dose of at least 90 mg/kg A1AT at least once weekly for at least an additional 4 weeks. In some embodiments, the following schedule is used: (a) administering a dose of at least 120 mg/kg A1AT to the subject at least one day prior to an HCT procedure; (b) administering a dose of at least 90 mg/kg A1AT to the subject twice weekly following HCT for at least 4 weeks, which may optionally be followed by a dose of at least 90 mg/kg A1AT once weekly for at least an additional 4 weeks. This A1AT dosage regime, in some embodiments, is given in combination with at least one immunosuppressive agent.

In some embodiments, part (a) above comprises administering a dose of 120, 130, 140, 150, 160, 170, 180, 190, 200, 220, 240, 260, 280, or 300 mg/kg A1AT to the subject at least one day prior to an HCT procedure. In some embodiments, more than one such dose can be administered prior to the HCT procedure, such as within 3 months, 2 months, 1 month, 14 days, or 7 days of the HCT procedure. In some embodiments, part (a) comprises administering a dose of at least 120 mg/kg A1AT to the subject one day, two days, or three days prior to an HCT procedure. In some such embodiments, a dose of at least 120 mg/kg A1AT is administered to the subject one day prior to an HCT procedure.

In some embodiments, part (b) above comprises administering a dose of 90, 100, 110, 120, 130, 140, 150, 160, 180, or 200 mg/kg A1AT to the subject twice weekly following HCT for at least 4 weeks. This is optionally followed by administering a dose of 90, 100, 110, 120, 130, 140, 150, 160, 180, or 200 mg/kg A1AT once weekly for at least an additional 4 weeks.

This disclosure also contemplates methods of reducing the risk of onset of acute graft versus host disease (aGVHD) in a subject receiving hematopoietic cell transplantation (HCT) comprising administering alpha-1 antitrypsin (A1AT) according to the following schedule: (a) administering a dose of 120 mg/kg A1AT to the subject one day prior to an HCT procedure; and (b) administering a dose of 90 mg/kg A1AT to the subject twice weekly following HCT for at least 4 weeks. This may optionally be followed by a dose of 90 mg/kg A1AT once weekly for at least an additional 4 weeks. And the above A1AT regime can optionally be given in combination with at least one immunosuppressive agent.

The disclosure further contemplates methods of reducing the risk of onset of acute graft versus host disease (aGVHD) in a subject receiving hematopoietic cell transplantation (HCT) comprising administering alpha-1 antitrypsin (A1AT) according to the following schedule: (a) administering a dose of 180 mg/kg A1AT to the subject one day prior to an HCT procedure; and (b) administering a dose of 120 mg/kg A1AT to the subject twice weekly following HCT for at least 4 weeks. This may optionally be followed by a dose of 120 mg/kg A1AT once weekly for at least an additional 4 weeks. And the above A1AT regime can optionally be given in combination with at least one immunosuppressive agent.

In any of the methods described above, administration of A1AT can continue for at least 100 days after an HCT procedure. In embodiments where an immunosuppressive is given, the subject may be administered at least one immunosuppressive agent comprising methylprednisone, methylprednisolone, or another steroid agent. In some cases the subject is administered 1-2 mg/kg methylprednisone or methylprednisolone per day following an HCT procedure. In some embodiments, the subject is administered at least one immunosuppressive agent comprising tacrolimus, cyclosporine, another calcineurin inhibitor, and/or methotrexate. In some embodiments, the subject is administered mycophenolate mofetil (MMF), an anti-TNF antibody, anti-lymphocyte globulin (ATG), and/or mesenchymal stem cells. In additional embodiments, the subject may be further administered one or more of pentostatin, ruxolitinib, brenbuximab vedotin (anti-CD30 antibody), tocilizumab (anti-IL6R antibody), an IL6 signaling inhibitor, mycophenolate mofetil (MMF), an anti-TNF antibody, basiliximab, daclizumab, inolimomab, alemtuzumab, etanercept, infliximab, a leukotriene antagonist, antilymphocyte globulin (ATG) such as horse ATG, and mesenchymal stem cells.

In some embodiments herein, the subject undergoes a myeloablative conditioning regimen. In other embodiments, the subject undergoes a reduced intensity conditioning regimen. In yet other embodiments, the subject does not undergo a conditioning regimen.

In some embodiments herein, the HCT procedure is an allogeneic HCT procedure comprising cells from (a) a related donor with at least one HLA mismatch or (b) an unrelated donor with or without at least one HLA mismatch. In some embodiments herein, the subject suffers from a leukemia, lymphoma, or myeloma. In other embodiments, the patient may suffer from a genetic hematopoietic disorder, such as thalassemia, sickle cell anemia, severe combined immunodeficiency, aplastic anemia, myelodysplastic syndrome. Furthermore, in embodiments herein, the patient may suffer from one or more of the following diseases or disorders, which may be treated with allogeneic HCT: acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), inborn errors of metabolism such as mucopolysaccharidosis, Gaucher disease, metachromatic leukodystrophy, adrenoleukodystrophy, epidermolysis bullosa, severe congenital neutropenia, Shwachman-Diamond syndrome, Diamond-Blackfan anemia, or leukocyte adhesion deficiency.

In some embodiments herein, the subject is at risk of developing Stage III or IV aGVHD following HCT.

In some embodiments, the median serum A1AT levels in the subject are above the normal human physiological levels on the day of the HCT procedure and remain above those levels for at least 28 days after the HCT procedure. In some embodiments, the peak serum A1AT levels in the subject are above normal mean human physiological levels on the day of the HCT procedure and remain above those levels for at least 28 days after the HCT procedure. In some embodiments, the median serum A1AT levels in the subject remain above 5.0 mg/mL on the day of the HCT procedure and for at least 28 days after the HCT procedure. In some embodiments, the peak serum A1AT levels in the subject remain above 5.0 mg/mL for at least 28 days after the HCT procedure. In some embodiments, the median serum A1AT levels in the subject remain above 4.0 mg/mL on the day of the HCT procedure and for at least 28 days after the HCT procedure. In some embodiments, the peak serum A1AT levels in the subject remain above 4.0 mg/mL for at least 28 days after the HCT procedure. In some embodiments, the median serum A1AT levels in the subject are above 3.5 mg/mL on the day of the HCT procedure and remain above 3.5 mg/mL for at least 28 days after the HCT procedure. In some embodiments, the peak serum A1AT levels in the subject are above 3.5 mg/mL on the day of the HCT procedure and remain above 3.5 mg/mL for at least 28 days after the HCT procedure. In some embodiments, the median serum A1AT levels in the subject remain above 3.0 mg/mL on the day of the HCT procedure and for at least 28 days after the HCT procedure. In some embodiments, the peak serum A1AT levels in the subject remain above 3.0 mg/mL for at least 28 days after the HCT procedure. In some embodiments, the median serum A1AT levels in the subject remain above 2.5 mg/mL on the day of the HCT procedure and for at least 28 days after the HCT procedure. In some embodiments, the peak serum A1AT levels in the subject remain above 2.5 mg/mL for at least 28 days after the HCT procedure. In some embodiments, the median serum A1AT levels in the subject remain above 2.0 mg/mL on the day of the HCT procedure and for at least 28 days after the HCT procedure. In some embodiments, the peak serum A1AT levels in the subject remain above 2.0 mg/mL for at least 28 days after the HCT procedure.

A method of treating acute graft versus host disease (aGVHD) in a subject following a hematopoietic cell transplantation (HCT) procedure, wherein the subject has been diagnosed following the HCT procedure with aGVHD, comprising administering a combination of a steroid and alpha-1 antitrypsin (A1AT) according to the following schedule: (a) administering the steroid to the subject; and (b) administering at least 90 mg/kg A1AT to the subject twice weekly following the aGVHD diagnosis for at least 4 weeks, optionally followed by a dose of at least 90 mg/kg A1AT once weekly for at least an additional 4 weeks. In some embodiments, part (b) comprises administering a dose of 90, 100, 110, 120, 130, 140, or 150 mg/kg A1AT to the subject twice weekly following HCT for at least 4 weeks optionally followed by a dose of 90, 100, 110, 120, 130, 140, or 150 mg/kg A1AT once weekly for at least an additional 4 weeks. In some embodiments, part (b) comprises administering a dose of at least 100 mg/kg A1AT to the subject twice weekly following HCT for at least 4 weeks followed by a dose of at least 100 mg/kg A1AT once weekly for at least an additional 4 weeks. In some embodiments, part (b) comprises administering a dose of 120 mg/kg A1AT to the subject twice weekly following HCT for at least 4 weeks followed by a dose of 120 mg/kg A1AT once weekly for at least an additional 4 weeks. In some embodiments, part (b) comprises administering a dose of at least 120 mg/kg A1AT to the subject twice weekly following HCT for at least 4 weeks followed by a dose of at least 90 mg/kg A1AT once weekly for at least an additional 4 weeks. In some embodiments, part (b) comprises administering a dose of at least 120 mg/kg A1AT to the subject twice weekly following HCT for at least 4 weeks followed by a dose of at least 100 mg/kg A1AT once weekly for at least an additional 4 weeks. In any of these above embodiments, administration of A1AT may continue for at least 100 days after an HCT procedure. In some embodiments, part (a) comprises administering the steroid at least once daily to the subject.

In some of the above embodiments, peak serum A1AT levels in the subject are above 3.5 mg/mL for at least 4 weeks after the first A1AT administration. Some embodiments further comprise determining whether the peak serum A1AT level in the subject is above 3.5 mg/mL following one or more administrations of A1AT, and, if the level is below 3.5 mg/mL, increasing the dose of A1AT administered to the subject. In some embodiments, dosage levels of A1AT given to a patient are chosen so as to be at or above a dosage level that has been shown to provide an average or median peak serum A1AT level in a group of previously tested clinical subjects of greater than or equal to 3.5 mg/mL. In some embodiments, the median serum A1AT levels in the subject are above the normal human physiological levels on the day of the HCT procedure and remain above those levels for at least 28 days after the HCT procedure. In some embodiments, the peak serum A1AT levels in the subject are above normal mean human physiological levels on the day of the HCT procedure and remain above those levels for at least 28 days after the HCT procedure.

In some embodiments, the first administration of A1AT is at a higher dose than the subsequent A1AT administrations during the first 4 weeks of treatment. In some such embodiments, the first administration of A1AT is at a dose of at least 120 mg/kg. In some such embodiments, the first administration of A1AT is at a dose of at least 180 mg/kg. In some embodiments, the first administration of A1AT is at a dose of 120, 130, 140, 150, 160, 170, 180, 200, or 220 mg/kg. In some embodiments, the first administration of A1AT is at a dose of 120, 130, 140, or 150 mg/kg. In some embodiments, the first administration of A1AT is at 120 mg/kg. In some embodiments, the first administration of A1AT is at 180 mg/kg.

In some embodiments, the steroid comprises prednisone, methylprednisone, or methylprednisolone. In some such embodiments, the steroid comprises prednisone, and the prednisone is administered at a daily dose of 0.5-3 mg/kg, 1-3 mg/kg, 1-2 mg/kg, 0.5 mg/kg, 1 mg/kg, 2 mg/kg, or 3 mg/kg. In some such embodiments, the steroid comprises methylprednisolone, and the methylprednisolone is administered at a daily dose of 0.5-3 mg/kg, 1-3 mg/kg, 1-2 mg/kg, 0.5 mg/kg, 1 mg/kg, 2 mg/kg, or 3 mg/kg. In some embodiments, the steroid comprises a topical steroid formulation, such as where the patient has Stage I aGVHD or otherwise has a significant maculopapular rash. In some embodiments, the steroid comprises a non-absorbable steroid, such as budesonide or beclomethasone, which, for example, may be added to a steroid regime or replaced for systemic steroids where a patient's aGHVD symptoms include GI tract involvement. In some embodiments, the subject is further administered at least one immunosuppressive agent comprising tacrolimus, cyclosporine, another calcineurin inhibitor, and/or methotrexate. In some embodiments, the subject is further administered mycophenolate mofetil (MMF), an anti-TNF antibody, antilymphocyte globulin (ATG), and/or mesenchymal stem cells. In additional embodiments, the subject may be further administered one or more of pentostatin, ruxolitinib, brenbuximab vedotin (anti-CD30 antibody), tocilizumab (anti-IL6R antibody), an IL6 signaling inhibitor, mycophenolate mofetil (MMF), an anti-TNF antibody, basiliximab, daclizumab, inolimomab, alemtuzumab, etanercept, infliximab, a leukotriene antagonist, antilymphocyte globulin (ATG) such as horse ATG, and mesenchymal stem cells.

In some embodiments, the subject undergoes a myeloablative conditioning regimen. In some embodiments, the subject undergoes a reduced intensity conditioning regimen.

In some embodiments, the HCT procedure is an allogeneic HCT procedure. In some embodiments, the allogeneic HCT procedure comprises cells from (a) a related donor with at least one HLA mismatch or (b) an unrelated donor with or without at least one HLA mismatch. In any of the embodiments above, the subject may suffer from leukemia, lymphoma, myeloma, a genetic hematopoietic disorder, such as thalassemia, sickle cell anemia, severe combined immunodeficiency, aplastic anemia, or myelodysplastic syndrome, or from acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), inborn errors of metabolism such as mucopolysaccharidosis, Gaucher disease, metachromatic leukodystrophy, adrenoleukodystrophy, epidermolysis bullosa, severe congenital neutropenia, Shwachman-Diamond syndrome, Diamond-Blackfan anemia, or leukocyte adhesion deficiency.

In any of the above methods, in some embodiments the subject does not have a genetic A1AT deficiency and/or has not previously received A1AT deficiency replacement therapy.

DETAILED DESCRIPTION

The section headings used herein are for organizational purposes only and are not to be construed as limiting the subject matter described. All references cited herein, including patent applications and publications, are incorporated herein by reference in their entireties for any purpose.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Système International de Unites (SI) accepted form. Numeric ranges are inclusive of the numbers defining the range. Measured values are understood to be approximate, taking into account significant digits and the error associated with the measurement.

The headings provided herein are not limitations of the various aspects of the disclosure, which can be had by reference to the specification as a whole. Accordingly, the terms defined immediately below are more fully defined by reference to the specification in its entirety.

As utilized in accordance with the present disclosure, the following terms, unless otherwise indicated, shall be understood to have the following meanings:

"Administering" refers to the physical introduction of a composition comprising a therapeutic agent to a subject, using any of the various methods and delivery systems known to those skilled in the art. General routes of administration for protein therapeutics include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Non-parenteral routes include a topical, epidermal or mucosal route of administration, for example, orally, intranasally, vaginally, rectally, sublingually or topically. Administering can also be performed, for example, once, a plurality of times, and/or over one or more extended periods.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"Alpha-1 antitrysin" abbreviated (A1AT), (A1-PI) or (AAT) herein includes a polypeptide comprising the full length human A1AT, which may be obtained from pooled human plasma, or which may be recombinant. It also includes a shorter human A1AT that retains a biological function such as protease inhibition (WO2010/088415) of the full length protein as well as fusion molecules comprising a human A1AT polypeptide. In some embodiments it includes AATs having no significant serine protease inhibitor activity (WO2010/088415). In some embodiments, the A1AT is a fusion molecule comprising an A1AT polypeptide and a fusion partner, optionally an Fc molecule, (e.g., an Fc fragment, an Fc analog, etc.), PEG, or albumin, such as an A1AT-Fc fusion molecule described in WO2013/106589 and WO2014/160768. In cases where the subject is non-human, the appropriate non-human A1AT may be used in lieu of human A1AT. In some embodiments, the A1AT comprises a signal polypeptide whereas in other embodiments it does not. In some embodiments, the A1AT comprises Zemaira® (CSL Behring), Prolastin® (Grifols), Prolastin® C (Grifols), Aralast® (Shire), Aralast NP® (Shire), Glassia® (Kamada), Trypsone® (Grifols), Alfalastin® (LFB Biomedicaments), or other commercial formulation or any combination thereof.

The terms "subject" and "patient" are used interchangeably herein to refer to a human unless the context makes it clear that a non-human subject or patient is intended (e.g. a "canine subject" or the like). In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

"Treatment," as used herein, refers to therapeutic treatment, for example, wherein the object is to slow down (lessen) an existing disease or disorder, as well as, for example, wherein the object is to prevent or delay the onset of symptoms of the disease or disorder in a patient who is at risk for developing the disease or disorder or to reduce the severity of the disease or disorder once it has begun.

"Reducing the risk of onset of" a disease or disorder is a type of treatment for the disease or disorder intended to reduce the risk that a subject who does not presently have the disease or disorder will develop the disease or disorder in the future, such as after an event like HCT or another non-organ or cellular transplantation.

The term "effective amount" or "therapeutically effective amount" refers to an amount of a drug effective to treat a disease or disorder in a subject or to reduce the risk of onset of the disease or disorder. In certain embodiments, an effective amount refers to an amount effective, at dosages and for periods of time necessary, to achieve the desired therapeutic result. A therapeutically effective amount of A1AT for example may vary according to factors such as the disease state, age, sex, and weight of the individual, and the ability of the antibody or antibodies to elicit a desired response in the individual.

"Hematopoietic cell transplantation" abbreviated HCT or HSCT is a procedure that comprises transplantation of hematopoietic stem cells or progenitor cells from a donor to a host or recipient, for example, with the goal of reestablishing immune cell function or bone marrow function.

"Graft versus host disease" abbreviated GVHD, occurs when immune cells such as immunocompetent T cells and natural killer (NK) cells in the donor transplant recognize host antigens as foreign and target them. Symptoms may range from rashes of the skin to systemic complications involving organs such as the gastrointestinal tract and liver.

GVHD may be either acute or chronic. "Acute GVHD" abbreviated aGVHD, may occur within the first 100 days after a transplantation procedure while chronic GHVD (cGVHD) may occur at later time points such as up to 12 months following a transplantation procedure.

Acute GVHD may be graded depending upon its severity and the extent of systemic involvement, such as Stage I, II, III, or IV (also called Grade I, II, III, or IV), with Stage IV being the most severe and having the highest risk of mortality.

An "immunosuppressive agent" herein broadly refers to any therapeutic agent intended to reduce an immune reaction in a patient.

GVHD may also be steroid-refractory. "Steroid-refractory acute GVHD" as used herein, for example, refers to aGVHD that does not improve despite treatment with steroids such as methylprednisone and methylprednisolone.

Hematopoietic Cell Transplantation (HCT)

HCT involves transplantation of hematopoietic cells such as stem cells and progenitor cells from a donor to a patient, for example, to reestablish immune cell function or bone marrow function in the patient. For example, hematopoietic stem and/or progenitor cells may be collected from bone marrow, peripheral blood or umbilical cord blood and infused into the patient.

The source of the transplanted cells may be from the patient to be treated ("autologous HCT"), for example, collected prior to a therapy that may act to destroy these cells such as myeloablative therapy or chemotherapy, and used where the patient's hematopoietic cells are otherwise healthy. In such cases, immunoreactions following treatment are relatively rare since the transplanted cells were originally taken from the patient. Alternatively, where the patient's own hematopoietic cells are diseased, for example, the donor cells are taken from a different human donor ("allogeneic HCT"), who may or may not be genetically related to the patient. Appropriate donors for allogeneic HCT may be identified, for example, through comparison of human leukocyte antigens (HLAs) of the donor versus recipient cells. A sibling or relative with an identical set of HLAs to the recipient is ideal, but, of course, not always available. A "syngeneic HCT" is a procedure in which the donor is an identical twin of the recipient. An unrelated donor, for example, identified through a database ideally will have no or only one HLA mismatch compared to the recipient. A greater degree of mismatch may be tolerated if circumstances otherwise warrant. In some cases, umbilical cord blood may be used as donor as it may be considered immunologically naïve compared to cells from an adult donor.

HCT procedures may be used as treatments for a variety of medical conditions such as cancers of immune origin, e.g. leukemia, lymphoma, and myeloma, and other diseases that result in abnormal hematopoiesis such as thalassemia, sickle cell anemia, severe combined immunodeficiency, aplastic anemia, myelodysplastic syndrome, and HIV-associated lymphomas, as well as for patients who are undergoing treatment (e.g. chemotherapy) for disorders where hematopoietic cells may be damaged by the disease treatment, such as neuroblastoma and germ cell tumors. Accordingly, in embodiments herein, the patient may suffer from a leukemia, lymphoma, or myeloma. In other embodiments, the patient may suffer from a genetic hematopoietic disorder, such as thalassemia, sickle cell anemia, severe combined immunodeficiency, aplastic anemia, myelodysplastic syndrome. Furthermore, in embodiments herein, the patient may suffer from one or more of the following diseases or disorders, which may be treated with allogeneic HCT: acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), inborn errors of metabolism such as mucopolysaccharidosis, Gaucher disease, metachromatic leukodystrophy, adrenoleukodystrophy, epidermolysis bullosa, severe congenital neutropenia, Shwachman-Diamond syndrome, Diamond-Blackfan anemia, or leukocyte adhesion deficiency. In some embodiments, patients having one of the above-listed diseases or disorders may receive an allogeneic HCT.

To attempt to avoid complications following an HCT procedure, the HCT patient may undergo various post-HCT drug regimens as well as particular pre-conditioning procedures. In some cases, the cellular transplant may be prepared in such a way as to reduce risks of transplanting immunocompetent T cells or cells that may trigger adverse reactions such as GVHD. Such procedures are described further below.

GVHD Following Transplantation

Both acute (a) and chronic (c) GVHD are potential complications of an HCT procedure, particularly an allogeneic HCT procedure. In spite of immunosuppressive treatments following HCT procedures, about 20-80% of allogeneic HCT recipients develop aGVHD following the procedure. (See, e.g., P. J. Martin et al. *Biol. Blood Marrow Transplant.* 18: 1150-63 (2012).) In general, GVHD is often considered acute if it occurs within 100 days of the HCT procedure.

The risk of GVHD is related to the source of the transplanted cells. In particular, the risk of GVHD may increase if there is an HLA mismatch between the donor and recipient and the risk is greater in the case of an unrelated donor compared to a matched, sibling donor. (See Id.) The risk of GVHD is also lower in transplants from umbilical cord blood compared to transplants taken from adult bone marrow or adult peripheral blood, perhaps due to the immaturity of the immune cells in umbilical cord blood. However, the use of umbilical cord blood may be limited due to its relatively low volume.

Acute GVHD following HCT may occur in various degrees of severity and may involve different bodily organs to different degrees. aGVHD may frequently affect the skin, liver, and gastrointestinal (GI) tract. aGVHD may be graded according to criteria set by the IMBTR, for example, depending on the severity of symptoms and whether the liver and/or GI tract are involved. (P. A. Rowlings et al., *Br. J. Haematol.* 97: 855-64 (1997).) For example, the grading system involves first grading the involvement of different organs. The impact on the skin may be graded on a 4-level scale by the extent of a skin rash (% of the body surface impacted) and whether a generalized erythroderma is present with or without bullae formation. The concentration of bilirubin may indicate extent of liver involvement. The extent to which diarrhea and abdominal pain occur may be used to indicate GI tract involvement. In general, Stage I aGVHD does not involve the liver or GI tract and comprises a skin rash but not generalized erythroderma or more serious symptoms. Stage II or higher aGVHD either involves generalized erythroderma (exfoliative dermatitis involving 90% or more of the skin) and/or liver and/or GI tract involvement. For example, a Stage II patient may have generalized erythroderma but no involvement of liver or the GI tract, or may have a systemic reaction including a less serious skin reaction along with liver and/or GI tract symptoms such as a high bilirubin concentration or significant diarrhea symptoms. A Stage III aGVHD patient may have both a generalized erythroderma and more significant liver and GI tract symptoms, while a Stage IV aGVHD patient may have severe skin rash involving bullae along with abdominal pain, severe diarrhea, and high bilirubin concentration, for instance.

The following table summarizes how aGVHD may be staged in some embodiments, herein:

TABLE 1

Exemplary determination of aGVHD stage (IMBTR criteria)

| Organ Stage | Skin | Liver (Bilirubin) | Upper GI | Lower GI (stool/day) |
|---|---|---|---|---|
| 0 | No active erythematous GVHD rash | <2 mg/dL | None or intermittent nausea or anorexia | <500 mL/day |
| 1 | Maculopapular rash <25% of body surface area (BSA) | 2-3 mg/dL | Persistent nausea, vomiting or anorexia (not related to drug toxicity) | 500-999 mL/day |
| 2 | Maculopapular rash 25-50% BSA | 3.1-6 mg/dL | | 1000-1500 mL/day |
| 3 | Maculopapular rash >50% BSA | 6.1-15 mg/dL | | >1500 mL/day |
| 4 | Generalized rash (>50% BSA) plus bullous formation and desquamation >5% BSA | >15 mg/dL | | Severe abdominal pain with or without ileus or grossly bloody stool, regardless of stool volume |

Overall clinical stage

| | |
|---|---|
| 0 | No stage 1-4 in any organ |
| 1 | Stage 1-2 skin and stage 0 liver, upper GI, and lower GI |
| 2 | Stage 3 skin; and/or stage 1 liver; and/or stage 1 upper GI; and/or stage 1 lower GI |
| 3 | Stage 2-3 liver and/or stage 2-3 lower GI, with stage 0-3 skin and/or stage 0-1 upper GI |
| 4 | Stage 4 skin, liver, or upper GI, with stage 0-1 upper GI |

GVHD in the upper GI may be confirmed in some cases by upper GI biopsy or colonoscopy.

Patient prognosis also significantly worsens with grade of aGVHD, with patients having Stage IV aGVHD having a less than 10% survival rate. (MC Pasquini, 2008.)

In some embodiments, aGVHD may be scored by criteria developed at the University of Minnesota, and published in M. L. MacMillan et al., *Biol. Blood Marrow Transplant.*, 21(4): 761-767 (2015). According to this scoring system, initial high-risk (HR) aGVHD is defined as either skin stage 4 (see table above), lower GI stage 3-4 (see table above) or liver stage 3-4 (see table above), or skin stage 3+ and either lower GI stage 2-4 or liver stage 2-4. Symptoms that do not meet these criteria may be classified as standard risk (SR) aGVHD. Accordingly, this system uses the IMBTR stages above to place aGVHD subjects into "high risk (HR)" or non-high risk, i.e., standard risk (SR) categories.

In spite of immunosuppressive treatments following HCT procedures, about 20-80% of allogeneic HCT recipients develop aGVHD following the procedure. (See, e.g., P. J. Martin et al. *Biol. Blood Marrow Transplant.* 18: 1150-63 (2012).) In any event, several immunosuppressive treatments are commonly used to treat GVHD in post-HCT patients. For example, current first-line therapy for aGVHD includes steroid treatment with methylpredisone or methylprednisolone, which may be administered for Grade II and higher aGVHD. There are various second-line therapies for patients who do not respond sufficiently to steroid treatment and are, thus, steroid-refractory. These include mycophenolate mofetil (MMF), anti-TNF antibodies or other antibody drugs such as antibodies binding to CD3, CD147 and IL-2, antilymphocyte globulin (ATG), mesenchymal stem cells, and methotrexate (MTX). Given the severity of higher grade aGVHD, however, further treatment options as well as procedures to reduce the risk of onset of aGVHD in HCT patients are needed.

Exemplary Methods of Reducing the Risk of Onset of aGVHD

Encompassed herein are methods of reducing the risk of onset of aGVHD in a subject by administering A1AT both before and after an HCT procedure. For example, in some embodiments, administration of A1AT begins one, two, or three days prior to the HCT procedure and continues for at least 4 weeks after the procedure, such as at least 8 weeks, at least 12 weeks, or at least 100 days, or at least 120 days following the HCT procedure. In some embodiments, administration of A1AT begins prior to the HCT procedure such as one, two, three, seven, ten, or fourteen days prior or 1 month, 2 months, or 3 months prior to the procedure, and then continues for at least 4 weeks after the procedure. As administration of A1AT begins prior to the HCT procedure, in some embodiments the subject does not have GVHD symptoms at the start of the administration period. Similarly, in some embodiments, the subject's individual risk of developing aGVHD after the HCT procedure cannot be determined prior to the procedure.

In some embodiments, the subject is administered A1AT according to the following schedule: (a) administering a dose of at least 120 mg/kg A1AT, such as 120, 130, 140, 150, 160, 170, 180, 190, 200, 220, 240, 260, 280, or 300 mg/kg, to the subject at least one day prior to an HCT procedure; and (b) administering a dose of at least 90 mg/kg A1AT, such as 90, 100, 110, 120, 130, 140, 150, 160, 180, or 200 mg/kg A1AT, to the subject twice weekly following HCT for at least 4 weeks. In some embodiments, this regime is then followed by a dose of at least 90 mg/kg A1AT, such as 90, 100, 110, 120, 130, 140, 150, 160, 180, or 200 mg/kg A1AT, once weekly for at least an additional 4 weeks. This procedure may optionally also involve administration of at least one immunosuppressive agent.

Specific administration schedules include (a) administering a dose of 120 mg/kg A1AT to the subject one day prior to an HCT procedure; and (b) administering a dose of 90, 100, 110, or 120 mg/kg A1AT to the subject twice weekly following HCT for at least 4 weeks, optionally followed by a dose of 90, 100, 110, or 120 mg/kg A1AT once weekly for at least an additional 4 weeks; as well as (a) administering a dose of 180 mg/kg A1AT to the subject one day prior to an HCT procedure; and (b) administering a dose of 100, 110, 120, 130, or 140 mg/kg A1AT to the subject twice weekly following HCT for at least 4 weeks, optionally followed by a dose of 100, 110, 120, 130, or 140 mg/kg A1AT once weekly for at least an additional 4 weeks; as well as (a) administering a dose of 150 mg/kg A1AT to the subject one day prior to an HCT procedure; and (b) administering a dose of 90, 100, 110, or 120 mg/kg A1AT to the subject twice weekly following HCT for at least 4 weeks, optionally followed by a dose of 90, 100, 110, or 120 mg/kg A1AT once weekly for at least an additional 4 weeks; as well as (a) administering a dose of 120 mg/kg A1AT to the subject one day prior to an HCT procedure; and (b) administering a dose of 90 mg/kg A1AT to the subject twice weekly following HCT for at least 4 weeks; as well as (a) administering a dose of 120 mg/kg A1AT to the subject one day prior to an HCT procedure; and (b) administering a dose of 90 mg/kg A1AT to the subject twice weekly following HCT for at least 4 weeks followed by a dose of 90 mg/kg A1AT once weekly for at least an additional 4 weeks; as well as (a) administering a dose of 150 mg/kg A1AT to the subject one day prior to an HCT procedure; and (b) administering a dose of 100 mg/kg A1AT to the subject twice weekly following HCT for at least 4 weeks; as well as (a) administering a dose of 150 mg/kg A1AT to the subject one day prior to an HCT procedure; and (b) administering a dose of 100 mg/kg A1AT to the subject twice weekly following HCT for at least 4 weeks followed by a dose of 100 mg/kg A1AT once weekly for at least an additional 4 weeks; as well as (a) administering a dose of 180 mg/kg A1AT to the subject one day prior to an HCT procedure; and (b) administering a dose of 120 mg/kg A1AT to the subject twice weekly following HCT for at least 4 weeks; as well as (a) administering a dose of 180 mg/kg A1AT to the subject one day prior to an HCT procedure; and (b) administering a dose of 120 mg/kg A1AT to the subject twice weekly following HCT for at least 4 weeks followed by a dose of 120 mg/kg A1AT once weekly for at least an additional 4 weeks. Any of these above schedules may be performed in combination with administration of at least one immunosuppressive agent.

Immunosuppressive agents administered following HCT may include steroids such as prednisone, methylprednisone or methylprednisolone, which are currently first-line therapies for treating aGVHD following HCT, additional steroids such as budesonide and beclomethasone, which may be administered when there is GI tract involvement, as well as other agents such as calcineurin inhibitors like tacrolimus, sirolimus, and cyclosporine or others, which may be administered with methotrexate in some cases. Other therapies such as pentostatin, ruxolitinib, brenbuximab vedotin (anti-CD30 antibody), tocilizumab (anti-IL6R antibody), an IL6 signaling inhibitor, mycophenolate mofetil (MMF), an anti-TNF antibody, basiliximab, daclizumab, inolimomab, alemtuzumab, etanercept, infliximab, a leukotriene antagonist, antilymphocyte globulin (ATG) such as horse ATG, and/or mesenchymal stem cells may also be administered in combination with A1AT in some embodiments. In some embodiments, subjects may be administered a combination of A1AT with steroid and an IL6 signaling inhibitor such as tocilizumab or another IL6 signaling inhibitor. In some embodiments, where methylprednisone or methylprednisolone are administered, they are administered at 1-3 mg/kg/day, or 1-2 mg/kg/day.

In some embodiments, the subject may have also undergone a conditioning regimen such as a myeloablative conditioning regimen or a reduced intensity conditioning regimen.

In some embodiments, the HCT procedure is an allogeneic HCT procedure comprising cells from (a) a related donor with at least one HLA mismatch or (b) an unrelated donor with or without at least one HLA mismatch. In some embodiments, the donor is a related donor with one HLA mismatch. In some embodiments, the donor is an unrelated donor without an HLA mismatch. In some embodiments, the donor is an unrelated donor with one HLA mismatch. In some embodiments, the donor cells are not from umbilical cord blood. In some embodiments, the donor cells are derived from bone marrow. In some embodiments, the cells are derived from peripheral blood.

In some embodiments, the subject suffers from a disease or disorder such as leukemia, lymphoma, or myeloma. In other embodiments, the patient may suffer from a genetic hematopoietic disorder, such as thalassemia, sickle cell anemia, severe combined immunodeficiency, aplastic anemia, myelodysplastic syndrome. Furthermore, in embodiments herein, the patient may suffer from one or more of the following diseases or disorders, which may be treated with allogeneic HCT: acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), inborn errors of metabolism such as mucopolysaccharidosis, Gaucher disease, metachromatic leukodystrophy, adrenoleukodystrophy, epidermolysis bullosa, severe congenital neutropenia, Shwachman-Diamond syndrome, Diamond-Blackfan anemia, or leukocyte adhesion deficiency.

In some embodiments, the subject is at risk of developing Stage III or IV aGVHD following HCT.

In some embodiments, the median serum A1AT levels in the subject are above the normal human physiological levels on the day of the HCT procedure and remain above those levels for at least 28 days after the HCT procedure. In some embodiments, the peak serum A1AT levels in the subject are above normal human physiological levels on the day of the HCT procedure and remain above those levels for at least 28 days after the HCT procedure. AAT levels in subjects without genetic deficiency are generally in the range of 1.5 to 3.5 mg/mL, but, as AAT is an acute-phase reactant, these levels can be increased transiently by at least 2-fold or even more, for example, in a physiological response to inflammation. (Silverman and Sandhaus, *N Engl J Med.* 2009 Jun. 25; 360(26):2749-57.) In some embodiments, the median serum A1AT levels in the subject remain above 2.5 mg/mL on the day of the HCT procedure and for at least 28 days after the HCT procedure. In some embodiments, the peak serum A1AT levels in the subject remain above 2.5 mg/mL for at least 28 days after the HCT procedure. In some embodiments, the median serum A1AT levels in the subject remain above 2.0 mg/mL on the day of the HCT procedure and for at least 28 days after the HCT procedure. In some embodiments, the peak serum A1AT levels in the subject remain above 2.0 mg/mL for at least 28 days after the HCT procedure. In some embodiments, the administration of A1AT is performed such that the median serum A1AT levels in the subject are above 3.0 mg/mL on the day of the HCT procedure and remain above 3.0 mg/mL for at least 28 days after the HCT procedure. In some embodiments, the administration is performed such that the peak serum A1AT levels in the subject are above 3.0 mg/mL on the day of the HCT procedure and remain above 3.0 mg/mL for at least 28 days after the HCT procedure. In some embodiments, the administration of A1AT is performed such that the median serum A1AT levels in the subject are above 3.5 mg/mL on the day of the HCT procedure and remain above 3.5 mg/mL for at least 28 days after the HCT procedure. In some embodiments, the administration is performed such that the peak serum A1AT levels in the subject are above 3.5 mg/mL on the day of the HCT procedure and remain above 3.5 mg/mL for at least 28 days after the HCT procedure. In some embodiments, the median serum A1AT levels in the subject remain above 4.0 mg/mL on the day of the HCT procedure and for at least 28 days after the HCT procedure. In some embodiments, the peak serum A1AT levels in the subject remain above 4.0 mg/mL for at least 28 days after the HCT procedure. In some embodiments, the median serum A1AT levels in the subject remain above 5.0 mg/mL on the day of the HCT procedure and for at least 28 days after the HCT procedure. In some embodiments, the peak serum A1AT levels in the subject remain above 5.0 mg/mL for at least 28 days after the HCT procedure.

In some embodiments, dosage levels of A1AT given to a patient are chosen so as to be at or above a dosage level that has been shown to provide an average or median peak serum A1AT level in a group of previously tested clinical subjects of greater than or equal to a particular threshold, such as 2.5 mg/mL, 3.0 mg/mL, 3.5 mg/mL, 4.0 mg/mL, 4.5 mg/mL, or 5 mg/mL. In some embodiments, pre- and post-HCT A1AT dosages are designed so as to be at or above a dosage level that has been shown to provide an overall average or median serum A1AT level in a group of previously tested clinical subjects of greater than 1.5 mg/mL, greater than 2.0 mg/mL, or between 1.5 and 3.5 mg/mL, or between 2 and 4 mg/mL.

In other methods herein, pre- and post-HCT A1AT dosages are designed to ensure that median serum A1AT levels remain above 2.0 mg/mL both on the day of the HCT procedure and for at least 28 days after the HCT procedure. For example, in some embodiments, A1AT dosing following the HCT procedure may be daily, every 2 days, every 3 days, every 7 days, every 10 days or every 14 days so long as the median serum levels of A1AT remain above 2.0 mg/mL for at least 28 days after the procedure. For instance, in some embodiments patients may experience a depletion of serum proteins such as A1AT, for example, as a result of developing aGVHD symptoms. In such a case, the portion of the dosage regime following the HCT procedure may need to be adjusted so as to maintain serum A1AT levels above the normal human serum level following the HCT procedure. In other cases A1AT levels may be relatively stable such that a less frequent dosing following the procedure can be used. For example, in some embodiments, A1AT dosing following the HCT procedure may be daily, every 2 days, every 3 days, every 7 days, every 10 days or every 14 days so long as the median serum levels of A1AT remain above 3.0 mg/mL for at least 28 days after the procedure. In other embodiments, A1AT dosing following the HCT procedure may be daily, every 2 days, every 3 days, every 7 days, every 10 days or every 14 days so long as the median serum levels of A1AT remain above 3.5 mg/mL for at least 28 days after the procedure. In other embodiments, A1AT dosing following the HCT procedure may be daily, every 2 days, every 3 days, every 7 days, every 10 days or every 14 days so long as the median serum levels of A1AT remain above 4.0 mg/mL for at least 28 days after the procedure. In other embodiments, A1AT dosing following the HCT procedure may be daily, every 2 days, every 3 days, every 7 days, every 10 days or every 14 days so long as the median serum levels of A1AT remain above 5.0 mg/mL for at least 28 days after the procedure.

In methods herein, the A1AT may be derived from pooled human plasma or may be recombinant. The A1AT may also be a fusion protein, for example, comprising a fusion partner of albumin, Fc, or polyethylene glycol. Certain A1AT products, including A1AT-Fc fusion proteins, are described in patent publications WO 2013/106589, WO 2006/133403, U.S. Pat. Nos. 9,457,070, 9,884,096, and WO 2013/003641. Several commercial therapeutic A1AT products are available, including Prolastin®, Prolastin® C, Glassia®, Aralast®, Aralast® NP, Zemaira®/Respreeza®, and Alfalastin® (LFB).

Exemplary Methods of Treating aGVHD Following HCT with A1AT and Steroids

The disclosure herein also includes methods of treating aGVHD following an HCT procedure, for example, upon initial diagnosis of aGVHD, with a combination of A1AT and at least one steroid. Acute GVHD may be diagnosed clinically at any time from completion of the HCT procedure to 100 days from the procedure. Late-onset aGVHD can also occur more than 100 days after HCT.

The at least one steroid may comprise, for example, prednisone, methylprednisone or methylprednisolone, and/or a non-absorbable oral steroid such as budesonide or beclomethasone. The A1AT may be administered twice weekly at a dose of, for example, 90, 100, 110, 120, 130, 140, 150, 160, 170, 180, 200, 220, or 240 mg/kg A1AT for at least 4 weeks following the initial aGVHD diagnosis, along with the steroid administration. In some embodiments, this twice-weekly regime is followed by administration of, for example, 90, 100, 110, 120, 130, 140, 150, 160, 180, or 200 mg/kg A1AT, once weekly for at least an additional 4 weeks, along with continuation of steroid administration. In some embodiments, the A1AT is administered twice weekly at a dose of at least 90 mg/kg for at least 4 weeks following the initial aGVHD diagnosis, along with the steroid administration. In some embodiments, the A1AT is administered twice weekly at a dose of at least 100 mg/kg for at least 4 weeks following the initial aGVHD diagnosis, along with the steroid administration. In some embodiments, the A1AT is administered twice weekly at a dose of at least 110 mg/kg for at least 4 weeks following the initial aGVHD diagnosis, along with the steroid administration. In some embodiments, the A1AT is administered twice weekly at a dose of at least 120 mg/kg for at least 4 weeks following the initial aGVHD diagnosis, along with the steroid administration. In some embodiments, upon at least a partial response (PR) after the first 4 weeks of treatment, the dosage frequency is reduced to once weekly at either the same dosage level or a reduced dosage level.

In some embodiments, the patient's blood or plasma is monitored to ensure that peak serum levels of A1AT remain at least at 3.5 mg/mL over the first 4 weeks (or 28 days) of A1AT administration, and a higher or more frequent dose of A1AT may be administered if peak A1AT levels fall below that threshold. In some embodiments, the first dose of A1AT or the first two doses may be a loading dose, i.e., a higher dose level than the subsequent doses. In some embodiments, a loading dose may be, for example, 120, 130, 140, 150, 160, 180, 200, or 220 mg/kg A1AT. In some embodiments, the combination of twice-weekly A1AT and steroid is continued for longer than 4 weeks, such as for 8, 10, 12, 14, 16, or 18 weeks, or for 60, 80, 100, 120, 140, 160, or 180 days. In some such embodiments, upon at least a partial response (PR) after the first 4 weeks of treatment, the dosage frequency is reduced to once weekly at either the same dosage level or a reduced dosage level. And in some such embodiments, upon at least a PR, the frequency of steroid dosage is also made longer and/or the steroid dosage reduced so as to taper the subject off from the A1AT and steroid. In some embodiments, the overall treatment regime lasts for 100, 120, 140, 160, or 180 days.

In some embodiments, the patient's peak serum levels of A1AT remain at least 3.0 mg/mL over the first 4 weeks (or 28 days) of treatment. In some embodiments, if the patient's peak serum levels of A1AT fall below 3.0 mg/mL during the first 4 weeks (or 28 days) of treatment, the dose of A1AT is increased until peak serum levels remain above 3.0 mg/mL. In some embodiments, peak serum levels of A1AT remain at least 3.5 mg/mL over the first 4 weeks (or 28 days) of treatment. In some embodiments, if peak serum levels of A1AT fall below 3.5 mg/mL during the first 4 weeks (or 28 days) of treatment, the dose of A1AT is increased until peak serum levels remain above 3.5 mg/mL. In some embodiments, peak serum levels of A1AT remain at least 4.0 mg/mL over the first 4 weeks (or 28 days) of treatment. In some embodiments, if peak serum levels of A1AT fall below 4.0 mg/mL during the first 4 weeks (or 28 days) of treatment, the dose of A1AT is increased until peak serum levels remain above 4.0 mg/mL. In some embodiments, peak serum levels of A1AT remain at least 4.5 mg/mL over the first 4 weeks (or 28 days) of treatment. In some embodiments, if peak serum levels of A1AT fall below 4.5 mg/mL during the first 4 weeks (or 28 days) of treatment, the dose of A1AT is increased until peak serum levels remain above 4.5 mg/mL. In some embodiments, peak serum levels of A1AT remain at least 5.0 mg/mL over the first 4 weeks (or 28 days) of treatment. In some embodiments, if peak serum levels of A1AT fall below 5.0 mg/mL during the first 4 weeks (or 28 days) of treatment, the dose of A1AT is increased until peak serum levels remain above 5.0 mg/mL.

In some embodiments, dosage levels of A1AT given to a patient are chosen so as to be at or above a dosage level that has been shown to provide an average or median peak serum A1AT level in a group of previously tested clinical subjects of greater than or equal to a particular threshold, such as 2.5 mg/mL, 3.0 mg/mL, 3.5 mg/mL, 4.0 mg/mL, 4.5 mg/mL, or 5 mg/mL. In some embodiments, A1AT dosages are designed so as to be at or above a dosage level that has been shown to provide an overall average or median serum A1AT level in a group of previously tested clinical subjects of greater than 1.5 mg/mL, greater than 2.0 mg/mL, or between 1.5 and 3.5 mg/mL, or between 2 and 4 mg/mL.

Any of the above schedules may also be performed in combination with administration of at least one immunosuppressive agent. Immunosuppressive agents administered following HCT may include a second steroid such as prednisone, methylprednisone, methylprednisolone, budesonide or beclomethasone, as well as other agents such as calcineurin inhibitors like tacrolimus, sirolimus, and cyclosporine or others, which may be administered with methotrexate in some cases. For example, the above A1AT dosing schedules may be added to a steroid treatment plan that is based on the patient's grade or stage of aGVHD and the location and type of symptoms (e.g. whether there is GI tract involvement or whether symptoms are primarily localized to the skin). For example, patients presenting Stage II aGVHD are often treated with systemic steroids such as methylprednisolone. Non-absorbable oral steroids may be added as local therapy or substituted for systemic steroids in cases where there is GI tract involvement or suspected GI tract infection. In contrast, patients presenting Stage I aGVHD, which, for example, may mostly present as a maculopapular rash without liver or GI tract involvement, may be treated with topical steroids or a combination of topical and systemic steroids.

Steroid regimens for Stage II to Stage IV aGVHD generally involve treatment with glucocorticoids such as prednisone, methylprednisone, methylprednisolone, and/or the non-absorbable glucocorticoids such as budesonide or beclomethasone, which may be added to the regimen or substituted for other steroids for patients with GI tract involvement. Oral beclomethasone, however, is generally not given if patients have a GI infection such as cytomegalovirus (CMV) colitis, or are suspected of having such an infection.

Accordingly, in methods herein, the at least one steroid may comprise, for example, prednisone, methylprednisone, or methylprednisolone, budesonide or beclomethasone, administered alone or in combination. Prednisone, methylprednisone, or methylprednisolone may be administered at a dose of, for example, between 0.5 and 3.0 mg/kg per day, such as 1-2.5 mg/kg/day. For example, prednisone may be dosed for systemic administration at 1 mg/kg, 1.5 mg/kg, 2 mg/kg, 2.5 mg/kg, or 3 mg/kg per day, or for example at 2-2.5 mg/kg per day. Methylprednisolone may be dosed systemically at a range of moderate to high dosages such as 1-20 mg/kg or 1-10 mg/kg per day, or at more moderate dosages or dose ranges such as 0.5-3 mg/kg, 0.5 mg/kg, 1 mg/kg, 1.5 mg/kg, 2 mg/kg, 2.5 mg/kg, or 3 mg/kg per day, or 1.5-2.5 mg/kg per day. In some embodiments, methylprednisolone may be administered at 2 mg/kg/day. In some embodiments, methylprednisolone may be administered at 1.5 mg/kg/day. In some embodiments, methylprednisolone may be administered at 1 mg/kg/day. Beclomethasone may be administered in dosages such as 5-10 mg/day, or 5, mg/day, 6 mg/day, 7 mg/day, 8 mg/day, 9 mg/day, or 10 mg/day. As noted above, once at least a partial response is achieved after 4 weeks, the dosage and frequency of the steroid may be slowly tapered down.

Other therapies may also be added to a regimen of steroid plus A1AT in some embodiments, such as pentostatin, ruxolitinib, brenbuximab vedotin (anti-CD30 antibody), tocilizumab (anti-IL6R antibody), an IL6 signaling inhibitor, mycophenolate mofetil (MMF), an anti-TNF antibody, basiliximab, daclizumab, inolimomab, alemtuzumab, etanercept, infliximab, a leukotriene antagonist, antilymphocyte globulin (ATG) such as horse ATG, and/or mesenchymal stem cells. In some embodiments, patients may be administered a combination of A1AT with steroid and an IL6 signaling inhibitor such as tocilizumab or another IL6 signaling inhibitor.

In some embodiments, the subject may have also undergone a conditioning regimen such as a myeloablative conditioning regimen or a reduced intensity conditioning regimen.

In some embodiments, the HCT procedure is an allogeneic HCT procedure comprising cells from (a) a related donor with at least one HLA mismatch or (b) an unrelated donor with or without at least one HLA mismatch. In some embodiments, the donor is a related donor with one HLA mismatch. In some embodiments, the donor is an unrelated donor without an HLA mismatch. In some embodiments, the donor is an unrelated donor with one HLA mismatch. In some embodiments, the donor cells are not from umbilical cord blood. In some embodiments, the donor cells are derived from bone marrow. In some embodiments, the cells are derived from peripheral blood.

In some embodiments, the subject suffers from a disease or disorder such as leukemia, lymphoma, or myeloma. In other embodiments, the patient may suffer from a genetic hematopoietic disorder, such as thalassemia, sickle cell anemia, severe combined immunodeficiency, aplastic anemia, myelodysplastic syndrome. Furthermore, in embodiments herein, the patient may suffer from one or more of the following diseases or disorders, which may be treated with allogeneic HCT: acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), inborn errors of metabolism such as mucopolysaccharidosis, Gaucher disease, metachromatic leukodystrophy, adrenoleukodystrophy, epidermolysis bullosa, severe congenital neutropenia, Shwachman-Diamond syndrome, Diamond-Blackfan anemia, or leukocyte adhesion deficiency.

In some embodiments, the subject is at risk of developing Stage III or IV aGVHD following HCT.

In methods herein, the A1AT may be derived from pooled human plasma or may be recombinant. The A1AT may also be a fusion protein, for example, comprising a fusion partner of albumin, Fc, or polyethylene glycol. Several commercial therapeutic A1AT products are available, including Prolastin®, Glassia®, Aralast®, and Zemaira®/Respreeza®.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: A Phase 2/3 Open-Label and Double-Blind Clinical Studies of A1AT for Reducing Risk of Onset of Acute GVHD in HCT Recipients A human clinical trial of A1AT in HCT recipients is planned in two parts, an open-label portion with two cohorts of 20 patients, cohorts 1 and 2, given two particular dosage regimes, followed by a double-blind and placebo-controlled trial of A1AT vs. placebo in 160 patients using the dosage regime chosen in the open-label portion of the trial. In the open-label portion, cohort 1 will be given 120 mg/kg A1AT (Zemaira®/Respreeza®) one day prior to an HCT procedure (day −1) and then will be given 90 mg/kg A1AT twice weekly until day 28, then 90 mg/kg A1AT once weekly until day 56. Cohort 2 will be given 180 mg/kg A1AT (Zemaira®/Respreeza®) one day prior to an HCT procedure (day −1) and then will be given 120 mg/kg A1AT twice weekly until day 28, then 120 mg/kg A1AT once weekly until day 56. Data from the two cohorts will be reviewed at least 100 days after the HCT procedures for all patients and a dosage regime for the double-blind portion of the trial will be selected based on the previously tested regimes. In these dosage regimes, sufficient A1AT may be given both prior to and following HCT such that either median or peak A1AT levels in patients exceed levels of A1AT in normal human peripheral blood.

Patients selected for the trial must have an age of at least 18 years for the open-label portion and at least 12 years for the double-blind portion. The trial will be restricted to patients who have received a myeloablative conditioning regimen. Since the conditioning regimen can impact risk of developing aGVHD, limiting variation in conditioning regimen may help to evaluate results. Patients must also receive HCT from either a) a related donor where there is one or two HLA mismatches (e.g., 6/8 or 7/8) or b) an unrelated donor with either an HLA match or a mismatch (e.g. 7/8). Patients receiving an umbilical cord blood transplant are excluded, as are patients given anti-T cell antibody therapy, and patients who have previously had an HCT.

Patients will also be treated with a standard immunosuppression regimen of tacrolimus and methotrexate in addition to the A1AT or placebo. The observed rate of aGVHD in patients receiving tacrolimus and methotrexate is about 40-60%. (M. Jagasia et al. *Blood* 119(1): 296-307 (2012); Pavletic & Fowler, 2012.) Patients who develop aGVHD in spite of the treatment regimen may further be treated with steroids. In the second phase of the trial, patients on placebo who develop aGVHD and who are treated with steroids but are refractory to the steroid treatment may be unblended so as to receive further treatment with A1AT.

The primary endpoint for both parts of the trial will be the frequency of Grade II or higher aGVHD within 100 days following HCT. aGVHD in patients is graded according to Table 1 provided earlier in this disclosure. Secondary endpoints will be the frequency of each of Grades II, III, and IV aGVHD within 100 days following HCT, incidence of chronic GVHD at days 180 and 365 after HCT, incidence of systemic infections at days 28, 60, 180, and 365, days to non-relapse mortality, and overall mortality at days 180 and 366. Other secondary endpoints include frequency of recurrence of primary malignancies at days 180 and 365, incidence of discontinuation of immune suppression at days 180 and 365, time to neutrophil engraftment, frequency of steroid-refractory aGVHD (Grade II-IV) that respond to treatment with A1AT at day 28, overall response rate (ORR) for subjects with steroid-refractory aGVHD at day 56, incidence of related adverse events, and pharmacokinetic parameters such as AUC, Cmax and trough.

Example 2: A Phase III Clinical Trial of A1AT for Treatment of High Risk aGVHD after HCT in Combination with Methylprednisolone A Phase III, multi-center, randomized, placebo-controlled clinical trial of A1AT plus methylprednisolone or placebo plus methylprednisolone is planned for patients in need of initial treatment following an HCT procedure for high risk aGVHD (see the clinical high risk aGVHD features under the Minnesota standards at the following URL: http://www (followed by) z (dot) umn (dot) edu (dot) MNAcuteGVHDRiskScore). Newly diagnosed adult (>12 years) male and non-pregnant female patients with high-risk aGVHD following allogeneic HCT will be included in the trial. A1AT is contraindicated in IgA deficient patients, however.

Patients with newly diagnosed aGVHD after HCT will be randomized to receive 120 mg/kg A1AT (Zemaira®) or placebo twice weekly in addition to methylprednisolone (MP) at 2 mg/kg/day. If the subject has a response (either complete response (CR) or partial response (PR)) at Day 28 after the start of treatment, the subject may receive an additional 4 weeks of treatment with AAT once weekly. If a subject has a response (either CR or PR) at Day 28 after the start of treatment, the subject may also receive less frequent doses of methylprednisolone. Patients will remain in follow up through a primary end-point of 6 months (180 days). Patients will be assessed for GVHD through 8 weeks (on treatment), then a minimum of every two weeks through 12 weeks (120 days), then monthly through to the 6 month end-point. The trial will include 110 patients, with 55 per treatment arm.

For this trial, A1AT (Zemaira®) is supplied as a sterile, white lyophilized powder in 1 g vials and is reconstituted in sterile water for injection at 50 mg/mL. The placebo product (AlbuRX®5), a commercial albumin product, is similarly diluted to a 1.2% albumin solution in 5% dextrose, and has been demonstrated to be a visual match for the A1AT solution at 50 mg/mL. An unblinded pharmacist will prepare the two solutions.

The A1AT will be dosed at 120 mg/kg twice weekly, followed optionally by once weekly dosing after the first 4 weeks (28 days). Dose modeling estimates that a dose of 120 mg/mL twice weekly should achieve plasma A1AT levels of at least 3.5 mg/mL, which may be sufficient to attenuate the inflammatory process of GVHD. Dosing is intended to achieve a targeted steady-state AAT level of greater than or equal to 3.5 mg/mL.

Study assessments will include assessments for safety, clinical activity, pharmacokinetics, and pharmacodynamics. Clinical assessments will include scoring of GVHD symptoms, for example, including assessment of skin rash, gastrointestinal symptoms such as diarrhea, vomiting, and nausea, as well as liver function.

The primary objectives of the trial include assessing the efficacy of A1AT in combination with MP in patients with newly diagnosed GVHD. Secondary objectives include assessing the safety of A1AT in the treatment of patients with newly diagnosed GVHD and assessing the pharmacokinetic profile. Primary end-points include overall response rate (ORR), complete response (CR), and partial response (PR) at day 28 following start of treatment, as well as GVHD-free, relapse-free survival (GRFS) at six months in patients with newly diagnosed GVHD receiving A1AT compared to placebo in combination with the standard of care MP treatment, such as a 25% increase in GRFS at 6 months compared to MP standard of care. Additional endpoints include non-relapse mortality at day 180, incidence of recurrence of primary malignancies through day 180, pharmacokinetic parameters, incidence of chronic GVHD at day 100 and at day 180, incidence of discontinuation of immune suppression at day 28, day 60, and day 180, incidence of systemic infections at day 28, day 60, and day 180, and incidence of related adverse events.

The invention claimed is:

1. A method of reducing the risk of onset of acute graft versus host disease (aGVHD) in a subject receiving hematopoietic cell transplantation (HCT) comprising administering alpha-1 antitrypsin (A1AT) according to the following schedule:
 (a) administering a dose of 180 mg/kg A1AT to the subject one day prior to an HCT procedure; and
 (b) administering a dose of 120 mg/kg A1AT to the subject twice weekly following HCT for at least 4 weeks optionally followed by a dose of 120 mg/kg A1AT at least once weekly for at least an additional 4 weeks;
 optionally in combination with at least one immunosuppressive agent,
 wherein the treatment reduces the risk of onset of chronic graft versus host disease (cGvHD) in the subject.

2. The method of claim 1, comprising (b) administering a dose of 120 mg/kg A1AT to the subject twice weekly following HCT for at least 4 weeks followed by a dose of 120 mg/kg A1AT at least once weekly for at least an additional 4 weeks.

3. The method of claim 1, wherein administration of A1AT continues for at least 100 days after an HCT procedure.

4. The method of claim 1, wherein the subject is administered (a) at least one immunosuppressive agent comprising methylprednisone, methylprednisolone, or another steroid agent; (b) 1-2 mg/kg methylprednisone or methylprednisolone per day following an HCT procedure; (c) at least one immunosuppressive agent comprising tacrolimus, cyclosporine, another calcineurin inhibitor, and/or methotrexate; or (d) mycophenolate mofetil (MMF), an anti-TNF antibody, antilymphocyte globulin (ATG), and/or mesenchymal stem cells.

5. The method of claim 1, wherein the subject undergoes a myeloablative conditioning regimen or a reduced intensity conditioning regimen.

6. The method of claim 1, wherein the HCT procedure is an allogeneic HCT procedure comprising cells from (a) a related donor with at least one HLA mismatch or (b) an unrelated donor with or without at least one HLA mismatch.

7. The method of claim 1, wherein the subject suffers from leukemia, lymphoma, myeloma, a genetic hematopoietic disorder, acute myeloid leukemia (AML), acute lymphoblastic leukemia (ALL), chronic myeloid leukemia (CML), chronic lymphoblastic leukemia (CLL), a myeloproliferative disorder, a myelodysplastic syndrome, multiple myeloma, non-Hodgkin lymphoma, Hodgkin disease, aplastic anemia, pure red cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis (HLH), or inborn errors of metabolism.

8. The method of claim 1, wherein the subject is at risk of developing Stage III or IV aGVHD following HCT.

9. The method of claim 1, wherein part (b) comprises administering a dose of 120 mg/kg A1AT to the subject twice weekly following HCT for at least 8 weeks.

10. The method of claim 1, wherein part (b) comprises administering a dose of 120 mg/kg A1AT to the subject twice weekly following HCT for at least 8 weeks followed by a dose of 120 mg/kg A1AT once weekly for at least an additional 4 weeks.

11. The method of claim 1, wherein part (b) comprises administering a dose of 120 mg/kg A1AT to the subject twice weekly following HCT for at least 12 weeks optionally followed by a dose of 120 mg/kg A1AT once weekly for at least an additional 4 weeks.

* * * * *